United States Patent
Handa et al.

(10) Patent No.: US 8,300,766 B2
(45) Date of Patent: Oct. 30, 2012

(54) RADIO TOMOGRAPHY IMAGING METHOD

(75) Inventors: Takanobu Handa, Hiroshima (JP);
Shuji Kaneko, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 159 days.

(21) Appl. No.: 12/674,957

(22) PCT Filed: Dec. 22, 2008

(86) PCT No.: PCT/JP2008/073296
§ 371 (c)(1),
(2), (4) Date: Aug. 19, 2010

(87) PCT Pub. No.: WO2010/073308
PCT Pub. Date: Jul. 1, 2010

(65) Prior Publication Data
US 2011/0129060 A1    Jun. 2, 2011

(51) Int. Cl.
*A61N 5/10* (2006.01)
(52) U.S. Cl. ............... 378/65; 378/207; 382/131
(58) Field of Classification Search .......... 378/65, 378/4, 207; 382/131
See application file for complete search history.

(56) References Cited

U.S. PATENT DOCUMENTS
6,466,638 B1 * 10/2002 Silver et al. .......... 378/4
7,570,734 B2 * 8/2009 Arai et al. .......... 378/207

FOREIGN PATENT DOCUMENTS
| JP | 2003-116832 | 4/2003 |
| JP | 2005-058758 | 3/2005 |
| JP | 3940747 | 4/2006 |
| JP | 2007-111314 | 5/2007 |

* cited by examiner

*Primary Examiner* — Glen Kao
(74) *Attorney, Agent, or Firm* — Wenderoth, Lind & Ponack, L.L.P.

(57) ABSTRACT

A radio tomography imaging method includes calculating a conversion function based on transmission images picked up by using radiation emitted from first and second radiation sources. A position of the second radiation source when the radiation has been emitted coincides with a position of the first radiation source when the radiation has been emitted, and one of the first and second radiation sources emits the radiation when the other emits the radiation, picking up a plurality of first reconfiguration transmission images and a plurality of second reconfiguration transmission images by using a plurality of first reconfiguration radiations and a plurality of second reconfiguration radiations simultaneously emitted from the first radiation source and the second radiation source. The plurality of first and second reconfiguration transmission images are then corrected based on the conversion function. The plurality of corrected transmission images are reconfigured into three-dimensional data.

15 Claims, 7 Drawing Sheets ured on the basis of a transmission image of the
subject.

RADIO TOMOGRAPHY IMAGING METHOD

TECHNICAL FIELD

The present invention relates to a radio tomography imaging method, and especially relates to a radio tomography imaging method used when three-dimensional data of a subject is reconfigured on the basis of a transmission image of the subject.

BACKGROUND ART

A cone beam CT (CBCT: Cone Beam Computed Tomography) apparatus is known which reconfigures three-dimensional CT data of an object on the basis of a plurality of transmission images picked up by using a conically-shaped (cone-shaped) X-ray irradiated from a radiation source which rotates around the object. Such a cone beam CT apparatus can generate the three-dimensional CT data in a short time without rotating the radiation source plural times. In a case of employing a patient being as an picked up object, the patient as the picked up object has to stop breathing during the pick-up, in order to obtain a high-precision image free from the blurring of the picked up object caused by a respiratory movement. It is desired to shorten the pick-up time of the transmission image to reduce a strain of the patient.

When a rotation speed of the radiation source is increased, the pick-up time of the cone beam CT apparatus can be shortened. In order to rotate the radiation source safely at a high speed, a device such as a rotating portion of a large-size detector needs to be safely accommodated in a protection cover, and thereby the apparatus will become large and complicated and accordingly will be expensive. It is desired to carry out the high-speed CBCT pick-up without increasing the rotation speed.

Japanese Patent No. 3,940,747 discloses an X-ray diagnostic apparatus which can reduce a rotation angle so as to be less than 180°. The X-ray diagnostic apparatus reconfigures the three-dimensional data of a specimen on the basis of a plurality of X-ray projection images picked up at different angles around the specimen. In the X-ray diagnostic apparatus, when a relation of $\beta > \alpha$ ($\alpha$ represents a spread angle of the X-ray beam) is satisfied, at least two pairs of imaging systems of an X-ray tube and an X-ray detector are provided to intersect at 90° with each other. A plurality of X-ray projection images are picked up at different angles in a range from 0° to $(90+\beta)°$ by one of the imaging systems, and a plurality of X-ray projection images are picked up at different angles in a range from 90° to $(180+\beta)°$ by the other one of the imaging systems. A sensitivity difference between the two imaging systems is calculated from two of the X-ray projection images picked up at the same angles in a range from 90° to $(90+\beta)°$ by two pairs of the imaging systems before injection of a contrast medium, the sensitivities of a plurality of X-ray projection images picked up by the pairs of the imaging systems after the injection of the contrast medium is corrected on the basis of the sensitivity difference. The three-dimensional data of the specimen is reconfigured from the plurality of X-ray projection images whose sensitivities have been corrected.

DISCLOSURE OF THE INVENTION

An object of the present invention is to provide a radio tomography imaging method of picking up transmission images used to form three-dimensional data of a target at a higher speed.

A radio tomography imaging method according to the present invention includes: picking up a first calibration transmission image by using a first calibration radiation emitted from a first radiation source supported by a movable gantry; picking up a second calibration transmission image by using a second calibration radiation emitted from a second radiation source supported by the gantry; calculating a conversion function based on the first calibration transmission image and the second calibration transmission image; picking up a plurality of first reconfiguration transmission images by using a plurality of first reconfiguration radiations emitted from the first radiation source when the first radiation source is positioned at a plurality of first positions different from each other, respectively; picking up a plurality of second reconfiguration transmission images by using a plurality of second reconfiguration radiations emitted from the second radiation source when the second radiation source is positioned at a plurality of second positions different from each other, respectively; correcting the plurality of second reconfiguration transmission images into a plurality of corrected transmission images based on the conversion function; and reconfiguring the plurality of first reconfiguration transmission images and the plurality of corrected transmission images into three-dimensional data. A position at which the second radiation source is positioned when the second calibration radiation has been emitted coincides with a position at which the first radiation source is positioned when the first calibration radiation has been emitted. The first radiation source emits a radiation when the second calibration radiation is emitted. The second radiation source emits a radiation when the first correction radiation is emitted. A plurality of first times when the plurality of first reconfiguration radiations are respectively emitted coincide with a plurality of second times when the plurality of second reconfiguration radiations are respectively emitted.

It is preferable that the plurality of first reconfiguration radiations include the first calibration radiation.

The plurality of second reconfiguration transmission images are corrected into the plurality of corrected transmission images through brightness conversion.

A frequency distribution in brightness of the transmission image corrected from the second calibration transmission image based on the conversion function coincides with a frequency distribution in brightness of the first calibration transmission image.

A radio tomography imaging method according to the present invention further includes: picking up another first correction transmission image by using another first calibration radiation emitted from the first radiation source; and picking up another second correction transmission image by using another second calibration radiation emitted from the second radiation source. A position at which the second radiation source is positioned when the other second calibration radiation has been emitted is different from a position at which the first radiation source is positioned when the first calibration radiation has been emitted, and coincides with a position at which the first radiation source is positioned when the other first calibration radiation has been emitted. The first radiation source emits a radiation when the other second calibration radiation has been emitted. The second radiation source emits a radiation when the other first calibration radiation has been emitted. The conversion function is calculated based on the other first correction transmission image and the other second correction transmission image, in addition to the first correction transmission image and the second correction transmission image.

The first calibration transmission image is picked up separately from the plurality of first reconfiguration transmission images.

A plurality of the first calibration transmission images are picked up by using a plurality of the first calibration radiations emitted from the first radiation source when the first radiation source is positioned at the plurality of second positions, respectively. A plurality of the second calibration transmission images are picked up by using a plurality of the second calibration radiations emitted from the second radiation source when the second radiation source is positioned on the plurality of second positions, respectively. The first radiation source emits a radiation when each of the plurality of second calibration radiations has been emitted. The second radiation source emits a radiation when each of the plurality of first calibration radiations has been emitted. One of the plurality of second reconfiguration transmission images picked up when the second radiation source is positioned at a predetermined position is corrected based on the conversion function which is calculated based on one of the plurality of first calibration transmission images picked up when the first radiation source is positioned at the predetermined position, and one of the plurality of second calibration transmission images picked up when the second radiation source is positioned at the predetermined position.

The radio tomography imaging method according to the present invention further includes: picking up a third calibration transmission image by using a third calibration radiation emitted from a third radiation source supported by the gantry; picking up a fourth calibration transmission image by using a fourth calibration radiation emitted from the second radiation source; calculating another conversion function based on the third calibration transmission image and the fourth calibration transmission image; picking up a plurality of third reconfiguration transmission images by using a plurality of third reconfiguration radiations emitted from the third radiation source when the third radiation source is positioned on a plurality of third positions different from each other, respectively; and correcting the plurality of third reconfiguration transmission images into a plurality of other corrected transmission images based on the conversion function and the other conversion function. A position at which the second radiation source is positioned when the fourth calibration radiation has been emitted coincides with a position at which the third radiation source is positioned when the third calibration radiation has been emitted. The first radiation source emits a radiation when the third calibration radiation is emitted. The second radiation source emits a radiation when the third calibration radiation is emitted. The third radiation source emits a radiation when the first calibration radiation is emitted, and emits a radiation when the second calibration radiation is emitted. A plurality of third times when a plurality of third reconfiguration radiations are emitted coincide with a plurality of first times, respectively. The three-dimensional data is reconfigured from the plurality of first reconfiguration transmission images, the plurality of corrected transmission images, and the plurality of other corrected transmission images.

A time period during which the plurality of first reconfiguration radiations and the plurality of second reconfiguration radiations are emitted includes a time period during which a therapeutic radiation is irradiated to the target in the plurality of first reconfiguration transmission images and the plurality of second reconfiguration transmission images.

A radiotherapy apparatus control apparatus according to the present invention controls a radiotherapy apparatus which includes a first radiation source supported by a movable traveling gantry, and a second radiation source supported by the traveling gantry. The radiotherapy apparatus control apparatus according to the present invention includes: a calibrating section configured to calculate a conversion function based on a first calibration transmission image picked up by using a first calibration radiation emitted from the first radiation source and a second calibration transmission image picked up by using a second calibration radiation emitted from the second radiation source; an imaging control section configured to pick up a plurality of first reconfiguration transmission images by using a plurality of first reconfiguration radiations emitted from the first radiation source when the first radiation source is positioned on a plurality of first positions different from each other and pick up the plurality of second reconfiguration transmission images by using a plurality of second reconfiguration radiations emitted from the second radiation source when the second radiation source is positioned on a plurality of second positions different from each other, respectively; a correcting section configured to correct the plurality of second reconfiguration transmission images into a plurality of corrected transmission images based on the conversion function, respectively; and a re-configuring section configured to reconfigure the plurality of first reconfiguration transmission images and the plurality of corrected transmission images into three-dimensional data. A position at which the second radiation source is positioned when the second calibration radiation has been emitted coincides with a position at which the first radiation source is positioned when the first calibration radiation has been emitted. The first radiation source emits a radiation when the second calibration radiation is emitted. The second radiation source emits a radiation when the first calibration radiation is emitted. A plurality of first times when the plurality of first reconfiguration radiations are emitted coincide with a plurality of second times when the plurality of second reconfiguration radiations are emitted, respectively.

It is preferable that the calibrating section corrects the plurality of second reconfiguration transmission images into the plurality of corrected transmission images through brightness conversion of the plurality of second reconfiguration transmission images.

The conversion function is calculated so that a frequency distribution in brightness of the transmission image corrected from the second calibration transmission image based on the conversion function coincides with a frequency distribution in brightness of the first calibration transmission images.

The radiotherapy apparatus further includes: a third radiation source supported by the gantry. The calibrating section calculates another conversion function based on a third calibration transmission image picked up by using the third calibration radiation emitted from the third radiation source, and a fourth calibration transmission image picked up by using a fourth calibration radiation emitted from the second radiation source. A position at which the second radiation source is positioned when the fourth calibration radiation is emitted coincides with a position at which the third radiation source is positioned when the third calibration radiation is emitted. The first radiation source emits a radiation when the third calibration radiation is emitted. The second radiation source emits a radiation when the third calibration radiation is emitted. The third radiation source emits a radiation when the first calibration radiation is emitted, and emits a radiation when the second calibration radiation is emitted. The imaging control section picks up a plurality of the third reconfiguration transmission images by using a plurality of third reconfiguration radiations emitted from the third radiation source when the third radiation source is positioned on a plurality of third positions different from each other. A plurality of third times when the plurality of third reconfiguration radiations are emitted coincide with the plurality of first times, respectively. The correcting section corrects the plurality of third reconfiguration transmission images into the plurality of other corrected transmission images respectively based on the conversion function and another conversion function. The re-configuring section reconfigures the three-dimensional data from the plurality of first reconfiguration transmission images, the plurality of corrected transmission images, and the plurality of other corrected transmission images.

It is preferable that the radiotherapy system according to the present invention includes the radiotherapy apparatus control apparatus and the radiotherapy apparatus according to the present invention.

It is preferable that the radiotherapy apparatus further includes a therapeutic radiation irradiating unit configured to irradiate a therapeutic radiation to a target in the plurality of first reconfiguration transmission images and the plurality of second reconfiguration transmission images. It is preferred that the therapeutic radiation irradiating unit is supported by the gantry.

BEST MODE FOR CARRYING OUT THE INVENTION

Figure 1:
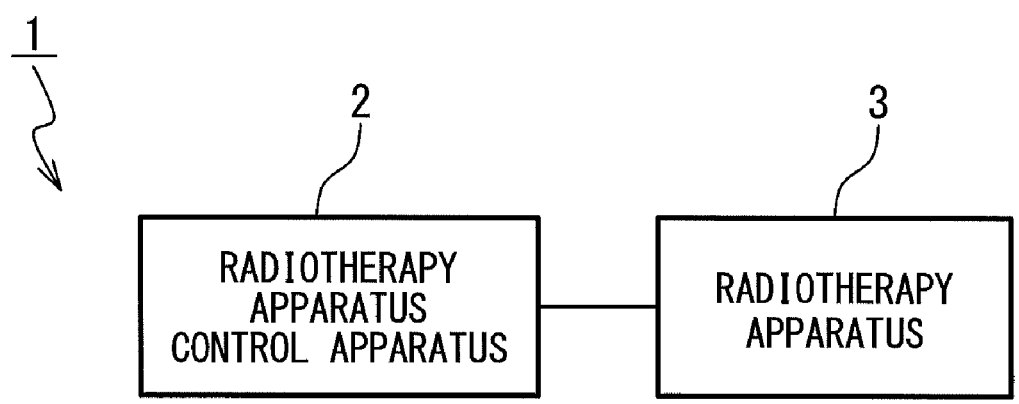
FIG. 1 is a block diagram showing a radiotherapy system according to an embodiment of the present invention.

Referring to drawings, a radiotherapy system according to embodiments of the present invention will be described. As shown in FIG. 1, the radiotherapy system 1 includes a radiotherapy apparatus control apparatus 2 and a radiotherapy apparatus 3. The radiotherapy apparatus control apparatus 2 is a computer exemplified by a personal computer. The radiotherapy apparatus control apparatus 2 and the radiotherapy apparatus 3 are connected with each other to bi-directionally transfer information.

Figure 2:
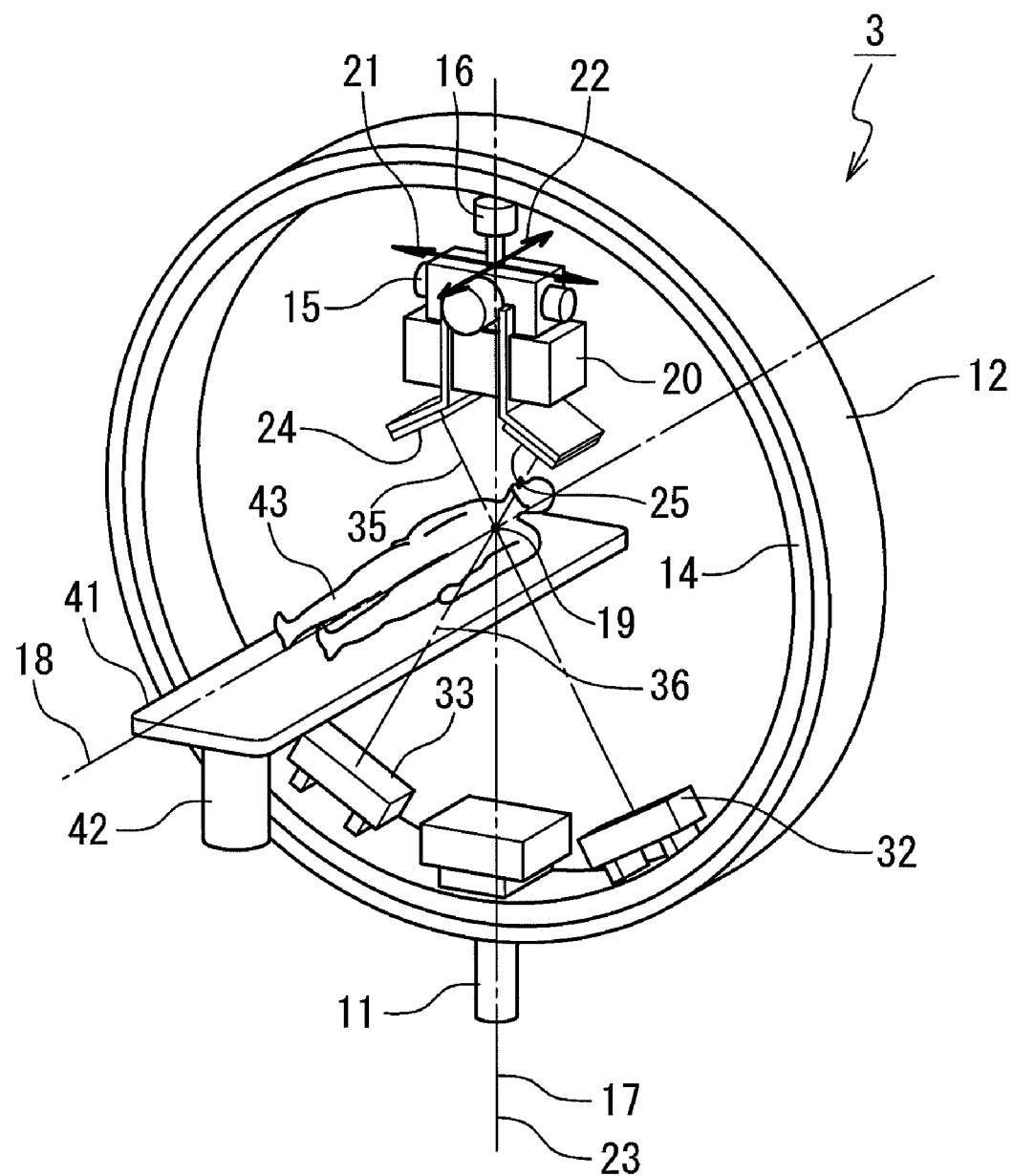
FIG. 2 is a perspective view showing a radiotherapy apparatus.

FIG. 2 shows the radiotherapy apparatus 3. The radiotherapy apparatus 3 includes a rotation driving unit 11, an O-ring 12, a traveling gantry 14, an swing mechanism 15, and a therapeutic radiation irradiating unit 16. The rotation driving unit 11 rotatably supports the O-ring 12 on a base around a rotation axis 17, and rotates the O-ring 12 around the rotation axis 17 under the control of the radiotherapy apparatus control apparatus 2. The rotation axis 17 is parallel to a vertical direction. The O-ring 12 is formed in a ring shape to have a rotation axis 18 at the center, and supports the traveling gantry 14 so that the traveling gantry 14 can rotate around the rotation axis 18. The rotation axis 18 is perpendicular to the vertical direction, and passes through an isocenter 19 included in the rotation axis 17. The rotation axis 18 is further fixed to the O-ring 12, namely, rotates around the rotation axis 17 together with the O-ring 12. The traveling gantry 14 is formed in a ring shape to have the rotation axis 18 at the center, and is arranged to form a concentric circle with the O-ring 12. The radiotherapy apparatus 3 further includes a travel driving unit (not shown). The travel driving unit rotates the traveling gantry 14 around the rotation axis 18 under the control of the radiotherapy apparatus control apparatus 2.

The swing mechanism 15 is fixed to the inside of the ring of the traveling gantry 14, and supports the irradiating unit 16 on the traveling gantry 14 so that the therapeutic radiation irradiating unit 16 can be arranged to the inside of the traveling gantry 14. The swing mechanism 15 has a tilt axis 21 and a pan axis 22. The pan axis 22 is fixed to the traveling gantry 14, and is parallel to the rotation axis 18 without intersecting with the rotation axis 18. The tilt axis 21 intersects with the pan axis 22 at a right angle. The swing mechanism 15 rotates the therapeutic radiation irradiating unit 16 around the pan axis 22 and rotates the therapeutic radiation irradiating unit 16 around the tilt axis 21 under the control of the radiotherapy apparatus control apparatus 2.

The therapeutic radiation irradiating unit 16 irradiates a therapeutic radiation 23 under the control of the radiotherapy apparatus control apparatus 2. The therapeutic radiation 23 is irradiated almost along a straight line passing through an intersection point where the pan axis 22 intersects with the tilt axis 21. The therapeutic radiation 23 is formed to have an even intensity distribution. The therapeutic radiation irradiating unit 16 includes an MLC (Multi-Leaf Collimator) 20. The MLC 20 partially shields the therapeutic radiation 23 to change a shape of an irradiation field in a case of irradiating the therapeutic radiation 23 to a patient under the control of the radiotherapy apparatus control apparatus 2. The therapeutic radiation irradiating unit 16 is supported by the traveling gantry 14 in this manner. Thus, if the therapeutic radiation irradiating unit 16 is once adjusted to face the isocenter 19 by the swing mechanism 15, the therapeutic radiation 23 almost constantly passes through the isocenter 19 even when the O-ring 12 is rotated by the rotation driving unit 11 or the traveling gantry 14 is rotated by the travel driving unit. That is, the traveling and rotation allow the irradiation of the therapeutic radiation 23 from an arbitrary direction to the isocenter 19.

The radiotherapy apparatus 3 further includes a plurality of imaging systems. That is, the radiotherapy apparatus 3 includes diagnostic X-ray sources 24 and 25 and sensor arrays 32 and 33. The diagnostic X-ray source 24 is supported on the traveling gantry 14. The diagnostic X-ray source 24 is arranged on the inside of the ring of the traveling gantry 14, and is arranged on a position where an angle between a line segment connecting the isocenter 19 to the diagnostic X-ray source 24 and a line segment connecting the isocenter 19 to the therapeutic radiation irradiating unit 16 is an acute angle. The diagnosis X-ray source 24 emits a diagnosis X-ray 35 to the isocenter 19 under the control of the radiotherapy apparatus control apparatus 2. The diagnosis X-ray 35 is emitted from one point included in the diagnosis X-ray source 24, and is a conically-shaped corn beam with the one point as an apex. A spread angle of the diagnosis X-ray 35 is 12°. The diagnostic X-ray source 25 is supported on the traveling gantry 14. The diagnostic X-ray source 25 is arranged on the inside of the ring of the traveling gantry 14, and is arranged at a position where an angle between a line segment connecting the isocenter 19 to the diagnostic X-ray source 25 and the line segment connecting the isocenter 19 to the therapeutic radiation irradiating unit 16 is an acute angle. The diagnostic X-ray source 25 is further arranged at a position where an angle between the line segment connecting the isocenter 19 to the diagnostic X-ray source 24 and the line segment connecting the isocenter 19 to the diagnostic X-ray source 25 is a right angle (90°). The diagnosis X-ray source 25 emits a diagnosis X-ray 36 to the isocenter 19 under the control of the radiotherapy apparatus control apparatus 2. The diagnosis X-ray 36 is emitted from one point included in the diagnosis X-ray source 25, and is a conically-shaped corn beam with the one point as an apex. The spread angle of the diagnosis X-ray 36 is 12°.

The sensor array 32 is supported on the traveling gantry 14. The sensor array 32 receives the diagnosis X-ray 35 that is emitted from the diagnosis X-ray source 24 and transmits through a region surrounding the isocenter 19, and generates a transmission image of a target. The sensor array 33 is supported on the traveling gantry 14. The sensor array 33 receives the diagnosis X-ray 36 that is emitted from the diagnosis X-ray source 25 and transmits through a region surrounding the isocenter 19, and generates a transmission image of the target. The transmission image is formed from a plurality of pixels arranged in a matrix. Each of the plurality of pixels is related to a brightness. The transmission image represents an image of the target by coloring each of the plurality of pixels with the brightness related to the pixel. An FPD (Flat Panel Detector) and an X-ray II (image Intensifier) are exemplified as the sensor arrays 32 and 33.

According to such imaging systems, a transmission images around the isocenter 19 can be generated on the basis of image signals obtained by the sensor arrays 32 and 33.

The radiotherapy apparatus 3 further includes a couch 41 and a couch driving unit 42. The couch 41 is used by a patient 43 to lie on it, who will be treated by the radiotherapy system 1. The couch 41 includes a fixture (not shown). The fixture fixes the patient on the couch 41 so that the patient cannot move on it. The couch driving unit 42 supports the couch 41 on the base, and moves the couch 41 under the control of the radiotherapy apparatus control apparatus 2.

Figure 3:
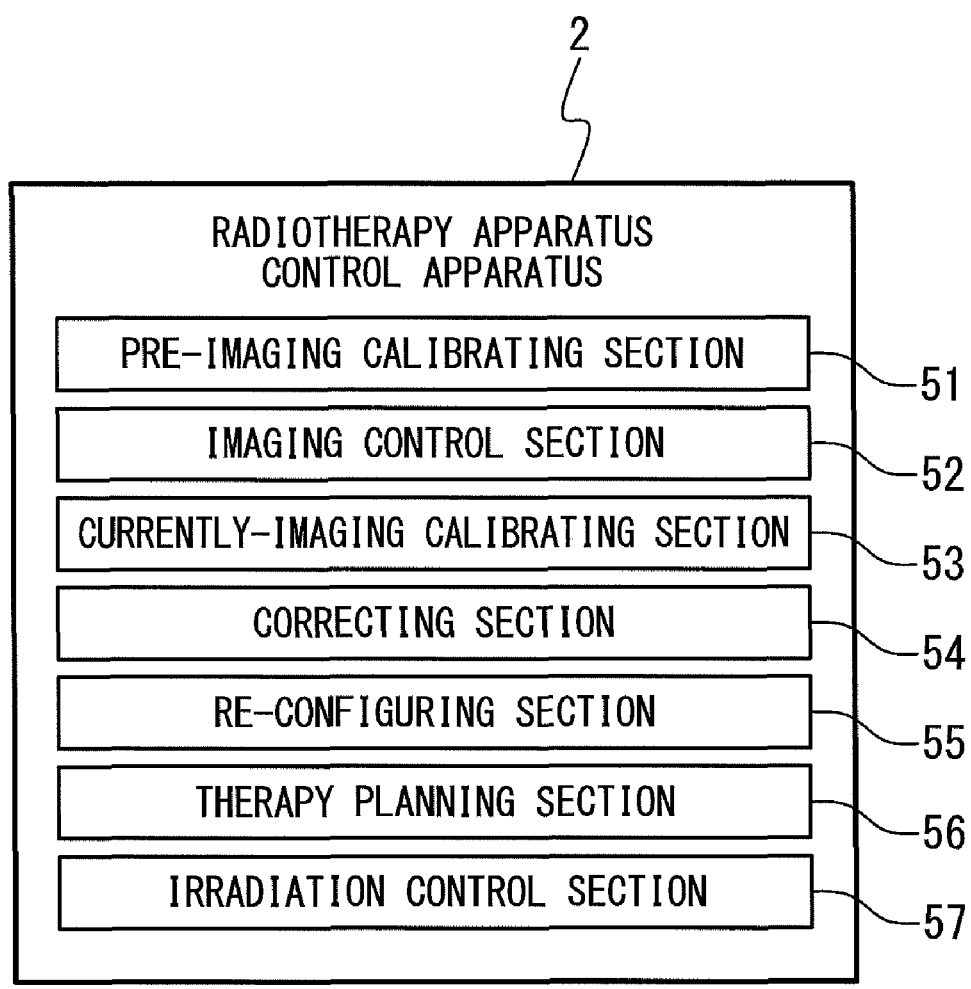
FIG. 3 is a block diagram showing a radiotherapy apparatus control apparatus.

FIG. 3 shows the radiotherapy apparatus control apparatus 2. The radiotherapy apparatus control apparatus 2 is a computer, and includes a CPU, a storage unit, an input unit, an output unit, and an interface, which are not shown. The CPU executes a computer program installed in the radiotherapy apparatus control apparatus 2 to control the storage unit, the input unit, and the output unit. The storage unit records the computer programs, and records data used by the CPU, and records data generated by the CPU. The input unit outputs data generated through an operation by a user to the CPU. A keyboard and a mouse are exemplified as the input unit. The output unit outputs data generated by the CPU to a user so that the data can be visible. A display is exemplified as the output unit. The interface outputs data generated by an external unit connected to the radiotherapy apparatus control apparatus 2 to the CPU, and outputs data generated by the CPU to the external unit. The external unit includes the rotation driving unit 11 of the radiotherapy apparatus 3, the travel driving unit, the swing mechanism 15, the therapeutic radiation irradiating unit 16, the MLC 20, the imaging systems (the diagnostic X-ray sources 24 and 25 and the sensor arrays 32 and 33), and the couch driving unit 42.

The computer program includes a pre-imaging calibrating section 51, an imaging control section 52, a currently-imaging calibrating section 53, a correcting section 54, a re-configuring section 55, a therapy planning section 56, and an irradiation control section 57.

The pre-imaging calibrating section 51 picks up a plurality of calibration transmission images of a specimen located at the isocenter 19 by using the imaging system of the radiotherapy apparatus 3 while the traveling gantry 14 is rotated by the travel driving unit of the radiotherapy apparatus 3. The pre-imaging calibrating section 51 calculates shift displacement correction amounts, rotation displacement correction amounts, and three-dimensional rotation displacement correction amounts on the basis of the plurality of calibration transmission images.

The imaging control section 52 controls the travel driving unit of the radiotherapy apparatus 3 to rotate the traveling gantry 14 around the rotation axis 18 by 102.0° from a predetermined angle. The imaging control section 52 further controls the imaging systems of the radiotherapy apparatus 3 to pick up a plurality of transmission images of a patient 43 every time the traveling gantry 14 rotates by 0.5°. That is, every time the traveling gantry 14 rotates by 0.5°, the imaging control section 52 control the diagnostic X-ray source 24 to emit the diagnostic X-ray 35 and the diagnostic X-ray source 25 to emit the diagnostic X-ray 36. At this time, the diagnostic X-ray 35 and the diagnostic X-ray 36 are simultaneously emitted every time the traveling gantry 14 rotates by 0.5°. Every time the traveling gantry 14 rotates by 0.5°, the imaging control section 52 further controls the sensor array 32 to pick up the transmission image of the patient 43 and the sensor array 33 to pick up the transmission image of the patient 43. That is, by the imaging control section 52, 205 transmission images are picked up by using the diagnostic X-rays 35 irradiated to the patient 43 from 205 directions different from each other, and 205 transmission images are picked up by using the diagnostic X-rays 36 irradiated to the patient 43 from 205 directions different from each other.

The currently-imaging calibrating section 53 calculates a brightness conversion function by using some of the plurality of transmission images picked up by the imaging control section 52 by using the diagnostic X-ray 35, and some of the plurality of transmission images picked up by the imaging control section 52 by using the diagnostic X-ray 36.

The correcting section 54 corrects the plurality of transmission images picked up by the imaging control section 52 into the shift displacement corrected transmission images on the basis of the shift displacement correction amounts calculated by the pre-imaging calibrating section 51. The correcting section 54 further corrects the shift displacement corrected transmission images into rotation displacement corrected transmission images on the basis of the rotation displacement correction amounts calculated by the pre-imaging calibrating section 51. The correcting section 54 corrects the rotation displacement corrected transmission images into three-dimensional rotation displacement corrected transmission images on the basis of the three-dimensional rotation displacement correction amounts calculated by the pre-imaging calibrating section 51. The correcting section 54 further corrects the three-dimensional rotation displacement corrected transmission images obtained from the plurality of transmission images picked up by the imaging control section 52 by using the diagnostic X-ray 36 into brightness corrected transmission images on the basis of the brightness conversion function calculated by the currently-imaging calibrating section 53.

The re-configuring section 55 reconfigures the plurality of brightness corrected images obtained by the correcting section 54 into the three-dimensional data. The three-dimensional data shows stereoscopic shapes of organs of the patient 43, and relates a plurality of transmittances to a plurality of voxels. The plurality of voxels are related to a plurality of rectangular parallelpipeds closely filling a space in which the patient 43 is located, respectively. As the rectangular parallelpiped, a 0.4-mm cube is exemplified. The transmittance corresponding to each of the voxels shows a transmittance of X-ray in the cube placed at a position corresponding to each of the voxels.

The therapy planning section 56 displays the three-dimensional data of the patient 43 reconfigured by the re-configuring section 55 on the output unit so that a user can view the data. The therapy planning section 56 further generates a therapeutic plan on the basis of data inputted by using the input unit. The therapeutic plan shows the three-dimensional data of the patient 43, and shows combinations of an irradiation angle and a dose. The irradiation angle shows a direction toward which the therapeutic radiation 23 is irradiated to an affected portion of the patient 43, and shows an O-ring rotation angle and a gantry rotation angle. The O-ring rotation angle indicates a position of the O-ring 12 with respect to the base. The gantry rotation angle indicates a position of the traveling gantry 14 with respect to the O-ring 12. The dose indicates a dose of the therapeutic radiation 23 irradiated from each of the irradiation angles to the patient 43.

The irradiation control section 57 carries out a moving-target tracking radiotherapy to the patient 43 by the radiotherapy apparatus 3 on the basis of the therapeutic plan generated by the therapy planning section 56, or carried out the Arc radiotherapy to the patient 43. When carrying out the moving-target tracking radiotherapy on the patient 43, the irradiation control section 57 calculates a position of the affected portion of the patient 43 on the basis of the transmission images picked up by the imaging systems of the radiotherapy apparatus 3. The irradiation control section 57 drives the therapeutic radiation irradiating unit 16 by using the swing mechanism 15 so that the therapeutic radiation 23 can transmit through the calculated position of the affected portion, and controls a shape of an irradiation field of the therapeutic radiation 23 by using the MLC 20. After driving the swing mechanism 15 and the MLC 20, the irradiation control section 57 controls the therapeutic radiation irradiating unit 16 to emit the therapeutic radiation 23. The irradiation control section 57 repeatedly performs the operations from the pick-up of the transmission images to the emission of the therapeutic radiation 23.

When the Arc radiotherapy is carried out to the patient 43, the irradiation control section 57 controls irradiation of the predetermined therapeutic radiation 23 to the patient 43 from each of the irradiation angles while the plurality of transmission images are picked up by the imaging control section 52, namely, while the traveling gantry 14 is rotated around the rotation axis 18.

Figure 4:
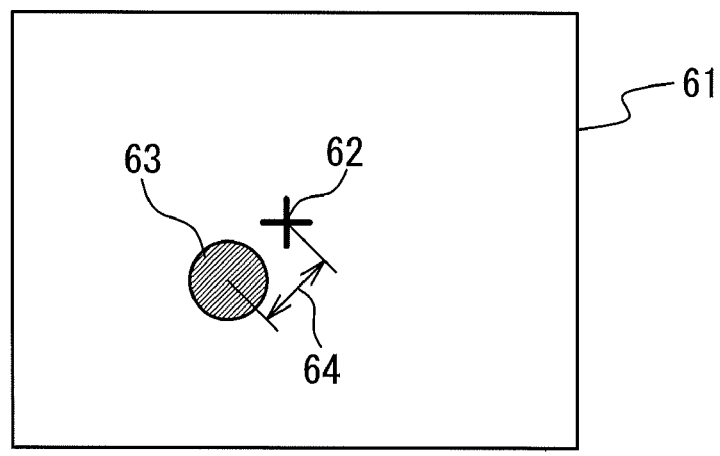
FIG. 4 is a diagram showing a transmission image used when a shift displacement correction amount is calculated.

FIG. 4 shows a transmission image used when the pre-imaging calibrating section 51 calculates the shift displacement amount. In a transmission image 61, a reference point 62 is set. As the reference point 62, a center of the transmission image 61 is exemplified. A figure 63 showing a sphere as a calibration specimen is shown on the transmission image 61. The sphere is arranged so that the center of the sphere can overlap with the isocenter 19. The pre-imaging calibrating section 51 calculates the shift displacement correction amount 64 on the basis of a position representing the figure 63 and the reference point 62 on the transmission image 61. The shift displacement correction amount 64 indicates a distance from the position representing the figure 63 to the reference position 62, and a direction of the reference point 62 with respect to the position representing the figure 63.

One of the plurality of shift displacement correction amounts 64 is calculated for every predetermined rotation angle of the traveling gantry 14 for each diagnostic X-ray source. That is, each of the plurality of shift displacement correction amounts 64 is related to a combination of the angle at which the traveling gantry 14 is directed and either one of the diagnostic X-ray sources 24 and 25. The angle indicates one of a plurality of angles at which the traveling gantry 14 can be directed when the traveling gantry 14 is rotated by 0.5°. Each of the plurality of shift displacement correction amounts 64 is calculated on the basis of the transmission image picked up by using the diagnostic X-ray emitted by the related diagnostic X-ray source when the traveling gantry 14 is directed to the related angle.

At this time, when the traveling gantry 14 is directed to a certain angle, the correcting section 54 corrects the transmission image obtained under the control of the imaging control section 52 by using the diagnostic X-ray emitted from the diagnostic X-ray source into the shift displacement corrected transmission image on the basis of the shift displacement correction amount 64 corresponding to the angle and the diagnostic X-ray source, so that the specimen arranged on the isocenter 19 can be shown at the reference point of the shift displacement corrected transmission image. Components of the radiotherapy apparatus 3 bend because of the rotation of the traveling gantry 14. For this reason, every time the traveling gantry 14 is rotated, the specimen arranged on the isocenter 19 is shown at a different position in the transmission image picked up by the imaging system. According to such a correction, a figure of the specimen arranged at the isocenter 19 is shown at the reference position in the shift displacement corrected transmission image, by rotating of the traveling gantry 14.

Figure 5:
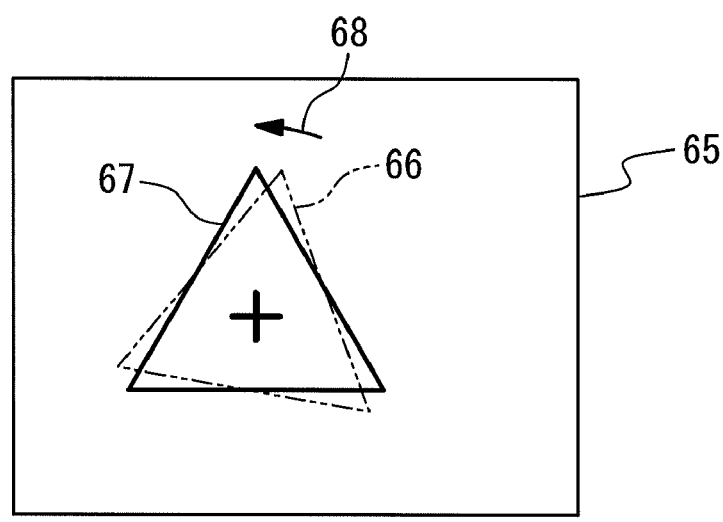
FIG. 5 is a diagram showing a transmission image used when a rotation displacement correction amount is calculated.

FIG. 5 shows a transmission image used when a rotation displacement amount is calculated by the pre-imaging calibrating section 51. A figure 66 indicating the specimen for calibration is shown in the transmission image 65. The specimen for calibration is formed in a shape different from the sphere, and is arranged so as to overlap with the isocenter 19. The pre-imaging calibrating section 51 calculates the rotation displacement correction amount 68 on the basis of an orientation of the figure 67 that has to be originally shown in the transmission image 65, and an orientation of the figure 66. The rotation displacement correction amount 68 shows an angle by which the figure 66 is rotated so that the orientation of the figure 66 can coincide with the orientation of the figure 67.

One of the plurality of rotation displacement correction amounts 68 is calculated for every predetermined rotation angle of the traveling gantry 14 for every diagnostic X-ray source. That is, each of the plurality of rotation displacement correction amounts 68 is related to a combination of an angle when the traveling gantry 14 is rotated, and either one of the diagnostic X-ray sources 24 and 25. When the traveling gantry 14 is rotated at the related angle, each of the plurality of rotation displacement correction amounts 68 is calculated on the basis of the transmission image picked up by using the diagnostic X-ray emitted from the related diagnostic X-ray source.

In this case, when the traveling gantry 14 is directed to the related angle, the correcting section 54 corrects the shift displacement corrected transmission image obtained by correcting the transmission image obtained under the control of the imaging control section 52 by using the diagnostic X-ray emitted from the diagnostic X-ray source into the rotation displacement corrected transmission image on the basis of the rotation displacement correction amount 68 related to the angle and the diagnostic X-ray source. The components of the radiotherapy apparatus 3 bend through the rotation of the traveling gantry 14. For this reason, every time the traveling gantry 14 is rotated, the specimen arranged on the isocenter 19 may be shown in the transmission image picked up by the imaging system in a rotated state. According to such a correction, in the rotation displacement corrected transmission image, a figure of the specimen arranged at the isocenter 19 is shown at a correct orientation through the rotation of the traveling gantry 14.

Figure 6:
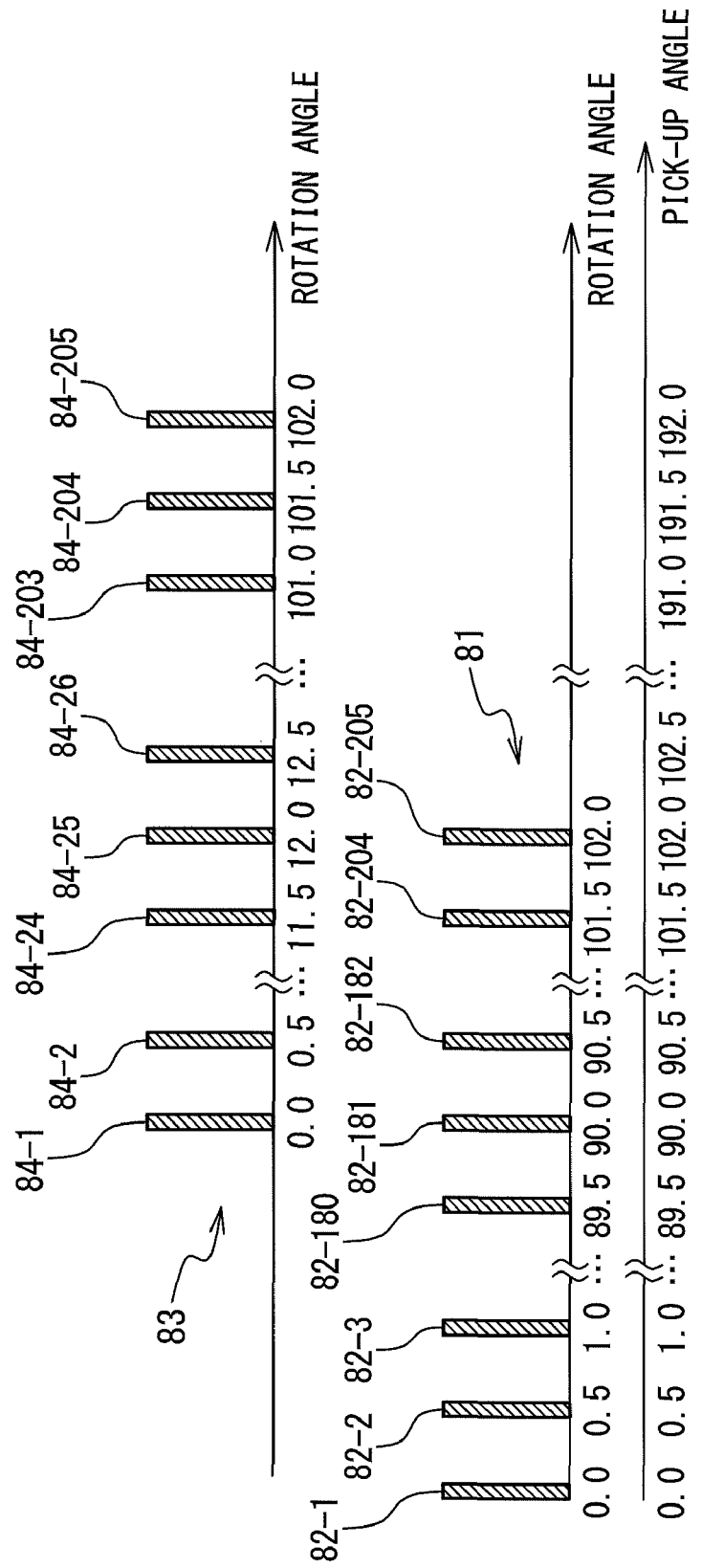
FIG. 6 is a diagram showing timings when two imaging systems pick up transmission images.

FIG. 6 shows a pick-up operation for obtaining the transmission images under the control of the imaging control section 52 by using the diagnostic X-ray source 35. The drawing shows that the pick-up operation 81 is performed when the traveling gantry 14 rotates from 0.0° to 102.0° and is formed from a plurality of pick-up operations 82-1 to 82-205. The pick-up operation 81 further shows that each pick-up operation 82-$i$ (i=1, 2, 3, . . . , 205) of the pick-up operations 82-1 to 82-205 is performed every time the traveling gantry 14 rotates by 0.5°. The pick-up operation 81 further shows that the pick-up operation 82-$i$ is performed when the traveling gantry 14 is rotated from 0.0° to (i×0.5−0.5)°. The pick-up operation 81 further shows that the pick-up operation 82-$i$ is performed when the diagnostic X-ray source 24 is positioned at (i×0.5−0.5)°, namely, the pick-up operation 82-$i$ is performed at the angle of (i×0.5−0.5)°. The angle shows a direction of a position on which the diagnostic X-ray source 24 is positioned, with respect to the isocenter 19, and is related to an angle of the traveling gantry 14 in one-to-one correspondence.

FIG. 6 further shows a pick-up operation for picking up the transmission images under the control of the imaging control section 52 by using the diagnostic X-ray 36. The drawing shows that the pick-up operation 83 is performed when the traveling gantry 14 rotates from 0.0° to 102.0° and is formed from pick-up operations 84-1 to 84-205 that the imaging control section 52 controls the pick-up of transmission images by using the diagnostic X-ray 36. The pick-up operation 83 further shows that each pick-up operation 84-$i$ (i=1, 2, 3, . . . , 205) of the pick-up operations 84-1 to 84-205 is performed every time the traveling gantry 14 rotates by 0.5°. The pick-up operation 83 further shows that the pick-up operation 84-$i$ is performed when the traveling gantry 14 is rotated to (i×0.5−0.5)°. The pick-up operation 83 further shows that the pick-up operation 84-$i$ is performed when the diagnostic X-ray source 25 is positioned at (i×0.5+89.5)° and shows that the pick-up operation 84-$i$ is performed at the angle of (i×0.5+89.5)°. The angle shows a direction of a position on which the diagnostic X-ray source 25 is positioned, with respect to the isocenter 19, and is related to an angle of the traveling gantry 14 in one-to-one correspondence.

The pick-up operation 81 and the pick-up operation 83 further show that the pick-up is duplicated by using both of the diagnostic X-ray 35 and the diagnostic X-ray 36 in a range of the pick-up angle from 90° to 102.0°, and shows that the angle for the pick-up operation 84-$j$ (j=1, 2, 3, . . . , 25) coincides with the angle for the pick-up operation 82-(j+180). The pick-up operation 81 and the pick-up operation 83 further show that the timing when the pick-up operation 84-$i$ is performed coincides with the timing when the pick-up operation 82-$i$ is performed.

Figure 7:
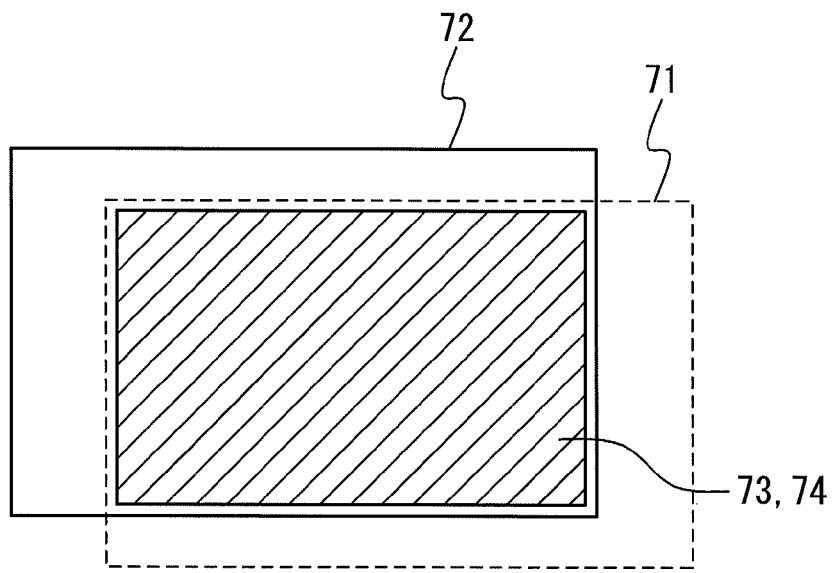
FIG. 7 is a diagram showing a field of view of the two imaging systems.

FIG. 7 shows a transmission image used when the brightness conversion function is calculated by the currently-imaging calibrating section 53. The transmission image 71 is picked up by using the diagnostic X-ray 35 when the diagnostic X-ray source 24 is positioned at a certain pick-up angle in a range from 90° to 102.0°, and shows a certain field of view. The transmission image 72 is picked up by using the diagnostic X-ray 36 when the diagnostic X-ray source 25 is positioned at the pick-up angle of the transmission image 71, and shows a certain field of view. Because of the bending of the components of the radiotherapy apparatus 3 caused by the rotation of the traveling gantry 14, the field of view of the transmission image 71 is different from the field of view of the transmission image 72 and a part of the field of view of the transmission image 71 overlaps with a part of the field of view of the transmission image 72. The transmission image 71 has a region 73 showing the overlapped field of view and the transmission image 72 has a region 74 showing the overlapped field of view.

Figure 8:
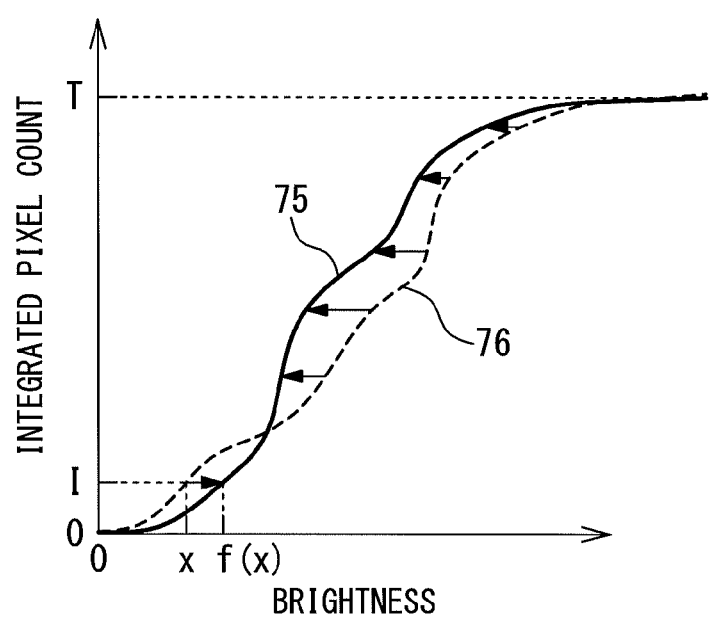
FIG. 8 is a diagram showing a cumulative frequency in brightness.

FIG. 8 shows a cumulative frequency distribution 75 and a cumulative frequency distribution 76 used when the brightness conversion function is calculated by the currently-imaging calibrating section 53. The cumulative frequency distribution 75 shows the cumulative frequency of a plurality of pixels included in the region 73 of the transmission 71 with respect to brightness. In this case, the cumulative frequency is related to the brightness in one-to-one correspondence. The cumulative frequency distribution 76 shows the cumulative frequency of a plurality of pixels included in the region 74 of the transmission 72 with respect to brightness. In this case, the cumulative frequency is related to the brightness in one-to-one correspondence.

The currently-imaging calibrating section 53 calculates the brightness conversion function on the basis of the cumulative frequency distribution 75 and the cumulative frequency distribution 76. The brightness conversion function relates brightness x corresponding to a cumulative frequency I in the cumulative frequency distribution 76 to brightness f(x) corresponding to a cumulative frequency I in the cumulative frequency distribution 75. That is, the brightness conversion function is calculated so that a frequency distribution of the brightness converted from the frequency distribution for the region 74 by use of the brightness conversion function can coincide with a frequency distribution of the brightness for the region 73.

The currently-imaging calibrating section 53 calculates such a brightness conversion function for each of 25 pairs of the transmission images picked up at duplicated pick-up angles under the control of the imaging control section 52 by using the diagnostic X-ray 35 and the diagnostic X-ray 36. The currently-imaging calibrating section 53 further calculates the brightness conversion function by averaging the 25 calculated brightness conversion functions.

The radio tomography imaging method according to an embodiment of the present invention is carried out by using the radiotherapy system 1, and includes an operation of the pre-imaging calibration, an operation for producing the three-dimensional data of the patient, an operation for generating a therapeutic plan, and an operation for carrying out the radiotherapy.

In the operation of the pre-imaging calibration, a user firstly arranges a sphere as a calibration specimen so that the center of the sphere can overlap with the isocenter 19. The user rotates the traveling gantry 14 around the rotation axis 18 by operating the radiotherapy apparatus control apparatus 2, picks up a transmission image of the sphere by using the diagnostic X-ray 35 emitted from the diagnostic X-ray source 24 every time the traveling gantry 14 rotates by 0.5°, and picks up the transmission image of the sphere by using the diagnostic X-ray 36 emitted from the diagnostic X-ray source 25.

The radiotherapy apparatus control apparatus 2 calculates the shift displacement correction amount on the basis of the picked up transmission image. The radiotherapy apparatus control apparatus 2 relates the calculated shift displacement correction amount to the rotation angle of the traveling gantry 14 and the diagnostic X-ray source, and records them in the storage unit.

The user arranges a calibration specimen formed in a shape other than the sphere so that the calibration specimen can overlap with the isocenter 19. The user rotates the traveling gantry 14 around the rotation axis 18 by operating the radiotherapy apparatus control apparatus 2, picks up a transmission image of the calibration specimen by using the diagnostic X-ray 35 emitted from the diagnostic X-ray source 24 every time the traveling gantry 14 rotates by 0.5°, and picks up a transmission image of the calibration specimen by using the diagnostic X-ray 36 emitted from the diagnostic X-ray source 25.

The radiotherapy apparatus control apparatus 2 calculates the rotation displacement correction amounts on the basis of the transmission image. The radiotherapy apparatus control apparatus 2 relates the calculated rotation displacement correction amount to the rotation angle of the traveling gantry 14 and the diagnostic X-ray source, and records them in the storage unit.

The user arranges a calibration specimen having at least four bodies that are not on an identical surface so that the calibration specimen can overlap with the isocenter 19. The user picks up a transmission image of the calibration specimen by using the diagnostic X-ray 35 emitted from the diagnostic X-ray source 24 and picks up a transmission image of the calibration specimen by using the diagnostic X-ray 36 emitted from the diagnostic X-ray source 25 by operating the radiotherapy apparatus control apparatus 2.

The radiotherapy apparatus control apparatus 2 calculates the three-dimensional rotation displacement correction amount on the basis of the transmission image. The radiotherapy apparatus control apparatus 2 relates the calculated three-dimensional rotation displacement correction amount to the diagnostic X-ray source, and records them in the storage unit.

In the operation for generating the three-dimensional data of the patient, the user firstly fixes the patient 43 on the couch 41 of the radiotherapy apparatus 3. The user operates the radiotherapy apparatus control apparatus 2, positions the O-ring 12 at a desired position by rotating the O-ring 12 around the rotation axis 17 by the rotation driving unit 11, rotates the traveling gantry 14 around the rotation axis 18 by using the travel driving unit to position the traveling gantry 14 at an initial angle (for example, 0.0°).

The radiotherapy apparatus control apparatus 2 rotates the traveling gantry 14 around the rotation axis 18 by 102.0° from the initial angle by using the travel driving unit of the radiotherapy device 3. The radiotherapy apparatus control apparatus 2 emits the diagnostic X-ray 35 by using the diagnostic X-ray source 24 and emits the diagnostic X-ray 36 by using the diagnostic X-ray source 25 every time the traveling gantry 14 rotates by 0.5°. At this time, the diagnostic X-ray 35 and the diagnostic X-ray 36 are simultaneously emitted every time the traveling gantry 14 rotates by 0.5°. In addition, the radiotherapy apparatus control apparatus 2 picks up a transmission image of the patient 43 by using the sensor array 32 and picks up a transmission image of the patient 43 by using the sensor array 33 every time the traveling gantry 14 rotates by 0.5°.

In such operations, the radiotherapy apparatus control apparatus 2 picks up the transmission images of the patient from 385 pick-up angles in units of 0.5° in a range from 0.0° to 192.0°. According to such operations, the radiotherapy apparatus control apparatus 2 can pick up the transmission images in a short time period as compared with a case of picking up a plurality of transmission images by using one imaging system.

In such operations, the radiotherapy apparatus control apparatus 2 duplicates the pick-up operation by using both of the diagnostic X-ray 35 and the diagnostic X-ray 36 in the pick-up angle range from 90° to 102.0°.

The radiotherapy apparatus control apparatus 2 calculates the cumulative frequency distribution 75 and the cumulative frequency distribution 76 in each of 25 pairs of the transmission images picked up at the duplicated pick-up angles by using the diagnostic X-ray 35 and the diagnostic X-ray 36. The radiotherapy apparatus control apparatus 2 calculates the brightness conversion function based on the cumulative frequency distribution 75 and the cumulative frequency distribution 76 in each of 25 pairs of the transmission images picked up at the duplicated pick-up angles. The radiotherapy apparatus control apparatus 2 further calculates the brightness conversion function by averaging the 25 calculated brightness conversion functions.

The radiotherapy apparatus control apparatus 2 corrects the transmission image into the shift displacement corrected transmission image on the basis of the shift displacement correction amount calculated in the operation of the pre-imaging calibration. The radiotherapy apparatus control apparatus 2 further corrects the shift displacement corrected transmission image into the rotation displacement corrected transmission image on the basis of the rotation displacement correction amount calculated in the operation of the pre-imaging calibration. The radiotherapy apparatus control apparatus 2 further corrects the rotation displacement corrected transmission image into the three-dimensional rotation displacement corrected transmission image on the basis of the three-dimensional rotation displacement correction amount calculated in the operation of the pre-imaging calibration.

The radiotherapy apparatus control apparatus 2 further corrects the three-dimensional rotation displacement corrected transmission images obtained from the transmission images picked up by using the diagnostic X-ray 36 into the brightness corrected transmission images on the basis of the brightness conversion functions. The transmission image picked up by using the diagnostic X-ray 35 is affected by a scattered radiation that the diagnostic X-ray 36 is emitted simultaneously with the diagnostic X-ray 35 and is scattered by the patient 43. In the same manner, the transmission image picked up by using the diagnostic X-ray 36 is affected by a scattered radiation that the diagnostic X-ray 35 is emitted simultaneously with the diagnostic X-ray 36 and is scattered by the patient 43. For this reason, the transmission image picked up by using the diagnostic X-ray 35 and the transmission image picked up by using the diagnostic X-ray 36 are different from each other in the image of the patient even when the pick-up angles are coincident. Since the brightness is corrected on the basis of a pair of transmission images picked up by using the diagnostic X-ray 35 and the diagnostic X-ray 36 which are emitted simultaneously, the brightness corrected transmission image corrected from the transmission image picked up by using the diagnostic X-ray 36 is almost coincident with the three-dimensional rotation displacement corrected transmission images corrected from the transmission images picked up by using the diagnostic X-ray 35 in the image of the patient.

The radiotherapy apparatus control apparatus 2 further reconfigures the three-dimensional rotation displacement corrected transmission images obtained from the transmission images picked up by using the diagnostic X-ray 35 and the brightness corrected transmission images obtained from the transmission images picked up by using the diagnostic X-ray 36 into the three-dimensional data of the patient 43.

According to such an operation for generating the three-dimensional data, degradation of the image quality caused by the sensitivity difference between the imaging systems can be minimized, and simultaneously the pick-up time of the transmission images required to reconfigure the three-dimensional data can be shortened without increasing the rotation speed of the traveling gantry 14. For example, in a case of rotating the traveling gantry 14 in the rotation speed of 7°/sec., the pick-up of the transmission images takes approximately 28 seconds when being picked up by one imaging system, and can be picked up for approximately 15 seconds in an actual operation. That is, such an operation for generating the three-dimensional data can reduce a time period during which the patient has to stop the breathing, to reduce a strain of the patient in the pick-up of the transmission images. Thus, the number of patients who can receive the therapy can be increased.

In the operation for generating the therapeutic plan, the user firstly supplies the three-dimensional data of the patient 43 generated by the operation for generating the three-dimensional data into the radiotherapy apparatus control apparatus 2. The radiotherapy apparatus control apparatus 2 generates an image showing the affected portion of the patient and organs surrounding the affected portion on the basis of the three-dimensional data. The user views the image by using the radiotherapy apparatus control apparatus 2 and specifies the position of the affected portion. The user further generates a therapy plan on the basis of the image and supplies the therapy plan into the radiotherapy apparatus control apparatus 2. The therapy plan shows the irradiation angles at which the therapeutic radiation is irradiated to the affected portion of the patient, and the dose and property of the therapeutic radiation irradiated from the respective irradiation angles.

In the operation for carrying out the radiotherapy, the radiotherapy apparatus control apparatus 2 controls the therapeutic radiation irradiating unit 16 to irradiate the therapeutic radiation 23 at the irradiation angles shown in the therapy plan generated in the operation for generating the therapy plan. That is, the radiotherapy apparatus control apparatus 2 positions the O-ring 12 at an O-ring rotation angle shown in the therapy plan by rotating the O-ring 12 around the rotation axis 17 by the rotation driving unit 11, and positions the traveling gantry 14 at a gantry rotation angle shown in the therapy plan by rotating the traveling gantry 14 around the rotation axis 18 by the travel driving unit of the radiotherapy apparatus 3.

The radiotherapy apparatus control apparatus 2 controls the imaging systems of the radiotherapy apparatus 3 to pick up the transmission image of the patient 43 after the therapeutic radiation irradiating unit 16 is driven. The radiotherapy apparatus control apparatus 2 calculates the position of the affected portion of the patient 43 on the basis of the transmission image. The radiotherapy apparatus control apparatus 2 drives the therapeutic radiation irradiating unit 16 by using the swing mechanism 15 so that the therapeutic radiation can transmit through the calculated position, and controls the shape of the irradiation field of the therapeutic radiation 23 by using the MLC 20. The radiotherapy apparatus control apparatus 2 controls the therapeutic radiation irradiating unit 16 to emit the therapeutic radiation 23 after driving the swing mechanism 15 and the MLC 20. The radiotherapy apparatus control apparatus 2 carries out such an operation repeatedly and periodically until the therapeutic radiation 23 of a dose shown in the therapy plan is irradiated to the affected portion of the patient 43. As the period, 0.2 seconds is exemplified.

It should be noted that so-called Arc radiotherapy in which the therapeutic radiation 23 is irradiated to the patient 43 while the traveling gantry 14 rotates, can be applied to the operation for carrying out the radiotherapy. In this case, the operation for carrying out the radiotherapy further may be carried out in parallel with the operation for generating the three-dimensional data.

In a case of the carrying out of such Arc radiotherapy in parallel with the operation for generating the three-dimensional data, it is possible to carry out a comparison with the position of the affected portion in the therapy plan by using the three-dimensional data generated through the operation for generating the three-dimensional data, and to confirm whether or not the Arc radiotherapy has been appropriately carried out.

Specifically, in the case that an angle range in which the traveling gantry 14 is rotated in the Arc radiotherapy is the same as an angle range in which the traveling gantry 14 is rotated in the three-dimensional data re-configuration, and when the three dimensional data clearly shows that the affected portion is positioned at an appropriate position, the user can determine that the affected portion has stayed at an appropriate position in the therapy. At that time, if the three-dimensional data unclearly shows the position of the affected portion, the user can determine that the affected portion has been moved from the appropriate position in the therapy. In such a case, when the three-dimensional data clearly shows that the affected portion stays at an inappropriate position, the user can determine that the affected portion is stayed at the inappropriate position in the therapy.

In a case that the angle range of the rotation of the traveling gantry 14 in the Arc therapy is narrower than the angle range of the rotation of the traveling gantry 14 in the three-dimensional data re-configuration and when the three-dimensional data clearly shows that the affected portion is positioned at the appropriate position, the user can determine that the affected portion stayed at the appropriate position in the therapy. In such a case, when the three-dimensional data unclearly shows the position of the affected portion, the user can determine that the affected portion may move from the appropriate position in the therapy. In such a case, when the three-dimensional data clearly shows that the affected portion is positioned at the inappropriate position, the user can determine that the affected portion stayed at the inappropriate position in the therapy.

In a case that the angle range of the rotation of the traveling gantry 14 in the Arc therapy is broader than the CBCT pick-up angle range of the rotation of the traveling gantry 14 in the three-dimensional data re-configuration and when the three-dimensional data clearly shows that the affected portion is positioned at the appropriate position, the user can determine that the affected portion stayed at the appropriate position only in the CBCT pick-up angle range in the therapy. In such a case, when the three-dimensional data unclearly shows the position of the affected portion, the user can determine that the affected portion moved from the appropriate position in the CBCT pick-up angle range. In such a case, when the three-dimensional data clearly shows that the affected portion is positioned at the inappropriate position, the user can determine that the affected portion stayed at the inappropriate position at least in the CBCT pick-up angle range.

It should be noted that when the spread angles of the diagnostic X-rays 35 and 36 are α°, the range of the pick-up angle is replaced from 192.0° to (180+α)°. At this time, the rotational angle range of the traveling gantry 14 required when the transmission images necessary for the re-configuration are picked up is replaced by (90+α)°. In such a case, in the same manner as that of the above-mentioned embodiment, the degradation of the image quality caused by the sensitivity difference in each of the plurality of imaging systems can be minimized, and simultaneously the pick-up time of the transmission images necessary to reconfigure the three-dimensional data can be shortened without increasing the rotation speed of the traveling gantry 14.

Moreover, the brightness conversion function does not have to be calculated on the basis of all of the 25 pairs of the transmission images, and for example, the brightness conversion function calculated on the basis of one pair of the transmission images among the 25 pairs of the transmission images can be used. In this case, the diagnostic X-ray source 24 and the diagnostic X-ray source 25 can be arranged at positions where an angle between a line segment connecting the isocenter 19 to the diagnostic X-ray source 24 and the line segment connecting the isocenter 19 to the diagnostic X-ray source 25 is (90+α/2)°. As the result, the rotation angle range of the traveling gantry 14 can be made narrow from (90+α)° to (90+α/2)°, and the transmission images necessary for the three-dimensional data can be picked up in a shorter period of time.

Figure 9:
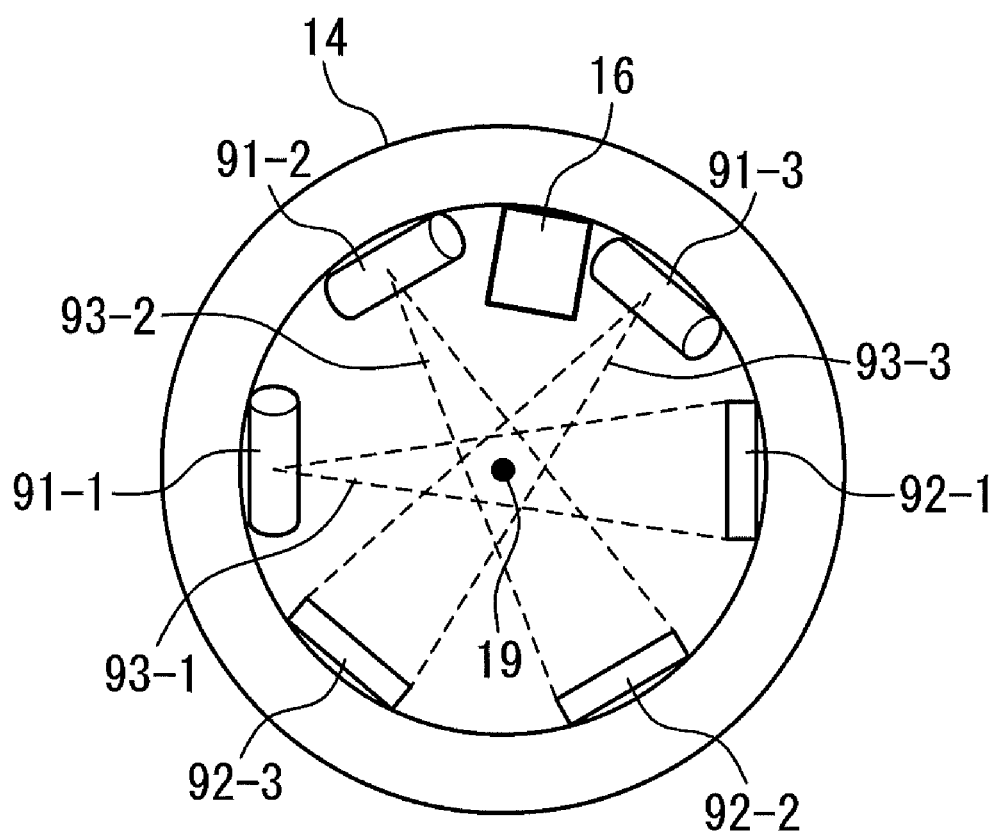
FIG. 9 is a diagram showing another radiotherapy apparatus.

The radio tomography imaging method according to the present invention can be also applied to another radiotherapy apparatus different from the radiotherapy apparatus 3 in the above-mentioned embodiment. FIG. 9 shows such a radiotherapy apparatus. In the radiotherapy apparatus, the imaging system of the radiotherapy apparatus 3 in the above-mentioned embodiment is replaced by another imaging system. Specifically, the radiotherapy apparatus includes diagnostic X-ray sources 91-1 to 91-3 and sensor arrays 92-1 to 92-3. The diagnostic X-ray sources 91-1 to 91-3 are supported by the traveling gantry 14, respectively, and are arranged to the inside of the ring of the traveling gantry 14. The diagnostic X-ray source 91-2 is arranged at a position where an angle between a line segment connecting the isocenter 19 to the diagnostic X-ray source 91-1 and a line segment connecting the isocenter 19 to the diagnostic X-ray source 91-2 is (180+α)°/3. The diagnostic X-ray source 91-3 is arranged at a position where an angle between a line segment connecting the isocenter 19 to the diagnostic X-ray source 91-2 and a line segment connecting the isocenter 19 to the diagnostic X-ray source 91-3 is (180+α)°/3. The diagnostic X-ray source 91-1 emits to the isocenter 19, the diagnostic X-ray 93-1 that is a cone-beam having the spread angle of α° under the control of the radiotherapy apparatus control apparatus 2. The diagnostic X-ray source 91-2 emits to the isocenter 19, the diagnostic X-ray 93-2 that is a cone-beam having the spread angle of α° under the control of the radiotherapy apparatus control apparatus 2. The diagnostic X-ray source 91-3 emits to the isocenter 19, the diagnostic X-ray 93-3 that is a cone-beam having the spread angle of α° under the control of the radiotherapy apparatus control apparatus 2.

The sensor arrays 92-1 to 92-3 are supported by the traveling gantry 14, respectively, and are arranged to the inside of the ring of the traveling gantry 14. The sensor array 92-1 receives the diagnostic X-ray 93-1 emitted by the diagnostic X-ray source 91-1 and transmits through the specimen surrounding the isocenter 19, and generates the transmission image of the specimen. The sensor array 92-2 receives the diagnostic X-ray 93-2 emitted by the diagnostic X-ray source 91-2 and transmits through the specimen surrounding the isocenter 19, and generates the transmission image of the specimen. The sensor array 92-3 receives the diagnostic X-ray 93-3 emitted by the diagnostic X-ray source 91-3 and transmits through the specimen surrounding the isocenter 19, and generates the transmission image of the specimen.

In the radio tomography imaging method according to the present invention, when the method is applied to such a radiotherapy apparatus, the operation for generating the three-dimensional data of the patient is replaced by another operation. In the operation, the user firstly fixes the patient 43 on the couch 41 of the radiotherapy apparatus. The user operates the radiotherapy apparatus control apparatus 2, arranges the O-ring 12 at a desired position by rotating the O-ring 12 around the rotation axis 17 by the rotation driving unit 11, rotates the traveling gantry 14 around the rotation axis 18 by using the travel driving unit to arrange the traveling gantry 14 at an initial angle (for example, 0.0°).

The radiotherapy apparatus control apparatus 2 rotates the traveling gantry 14 around the rotation axis 18 by (180+α)°/3 from the initial angle by using the travel driving unit of the radiotherapy device. The radiotherapy apparatus control apparatus 2 emits the diagnostic X-ray 93-1 by using the diagnostic X-ray source 91-1, emits the diagnostic X-ray 93-2 by using the diagnostic X-ray source 91-2, and emits the diagnostic X-ray 93-3 by using the diagnostic X-ray source 91-3. At this time, the diagnostic X-rays 93-1 to 93-3 are simultaneously emitted every time the traveling gantry 14 rotates by 0.5°. In addition, the radiotherapy apparatus control apparatus 2 picks up a transmission image of the patient 43 by using the sensor arrays 92-1 to 92-3 every time the traveling gantry 14 rotates by 0.5°.

In such operations, the radiotherapy apparatus control apparatus 2 picks up the transmission images of the patient at the pick-up angles varied 0.5° by 0.5° in a range from 0.0° to (180+α)°. According to such operations, the radiotherapy apparatus control apparatus 2 can image the transmission images in a short period of time, as compared with a case of picking up the transmission images by using two imaging systems.

In the same manner as that of the above-mentioned embodiment, the radiotherapy apparatus control apparatus 2 calculates a first brightness conversion function on the basis of a pair of the transmission images picked up at duplicated pick-up angles by using the diagnostic X-ray 93-1 and the diagnostic X-ray 93-2. Additionally, in the same manner as that of the above-mentioned embodiment, the radiotherapy apparatus control apparatus 2 calculates a second brightness conversion function on the basis of a pair of the transmission images picked up at duplicated pick-up angles by using the diagnostic X-ray 93-2 and the diagnostic X-ray 93-3.

The radiotherapy apparatus control apparatus 2 corrects the plurality of transmission images into the three-dimensional rotation displacement corrected transmission image on the basis of the shift displacement correction amount, rotation displacement correction amount, and three-dimensional rotation displacement correction amount calculated in the operation of the pre-imaging calibration.

Moreover, the radiotherapy apparatus control apparatus 2 corrects the three-dimensional rotation displacement corrected transmission image obtained from the plurality of transmission images picked up by using the diagnostic X-ray 93-2 into a first brightness corrected transmission image on the basis of the first calculated brightness conversion function. Furthermore, the radiotherapy apparatus control apparatus 2 corrects the three-dimensional rotation displacement corrected transmission image obtained from the plurality of transmission images picked up by using the diagnostic X-ray 93-3 into a second brightness corrected transmission image on the basis of the second calculated brightness conversion function.

Additionally, the radiotherapy apparatus control apparatus 2 reconfigures the first brightness corrected transmission image, the second brightness corrected transmission image, and the three-dimensional rotation displacement corrected transmission image obtained from the plurality of transmission images picked up by using the diagnostic X-ray 93-1 into the three-dimensional data of the patient 43.

According to the operation for generating such three-dimensional data, in the same manner as the radio tomography imaging method in the above-mentioned embodiment, degradation of the image quality caused by the sensitivity difference in each of the plurality of imaging systems can be minimized, and simultaneously the pick-up time of the plurality of transmission images required to reconfigure the three-dimensional data can be shortened without increasing the rotation speed of the traveling gantry 14, compared to a case of using two imaging systems. As the result, the operation for generating such a three-dimensional data can reduce a period of time during which the patient has to stop the breathing, can reduce a strain of the patient in the pick-up of the plurality of transmission images, and can increase the number of patients who can accept the therapy.

The radio tomography imaging method according to the present invention can be also applied to the radiotherapy apparatus having n imaging systems. In this case, n diagnostic X-ray sources are arranged at positions where an angle between two lines connecting two adjacent sources of the n diagnostic X-ray sources to the isocenter 19 is $(180+\alpha)°/n$.

In the radio tomography imaging method according to the present invention, when the method is applied to such a radiotherapy apparatus, the operation for generating the three-dimensional data of the patient is replaced by another operation. The radiotherapy apparatus control apparatus 2 rotates the traveling gantry 14 around the rotation axis 18 by $(180+\alpha)°/n$ from the initial angle by using the travel driving unit of the radiotherapy apparatus. The radiotherapy apparatus control apparatus 2 simultaneously emits the diagnostic X-ray from the n diagnostic X-ray sources every time the traveling gantry 14 rotates by 0.5°, and picks up the transmission image of the patient 43.

In the same manner as that of the above-mentioned embodiment, the radiotherapy apparatus control apparatus 2 calculates the plurality of brightness conversion functions on the basis of one pair of the transmission picks up picked up at the same pick-up angle by using two diagnostic X-rays emitted from the two adjacent diagnostic X-ray sources.

The radiotherapy apparatus control apparatus 2 corrects the plurality of transmission images into the three-dimensional rotation displacement corrected transmission image on the basis of the shift displacement correction amount, the rotation displacement correction amount, and the three-dimensional rotation displacement correction amount calculated through the operation of the pre-imaging calibration.

In addition, in order to match the frequency distribution of the brightness with the transmission image picked up by using one of the n diagnosis X-ray sources, the radiotherapy apparatus control apparatus 2 corrects the transmission image picked up by using the diagnosis X-ray sources except for the used source of the n number of the diagnosis X-ray sources. Moreover, the radiotherapy apparatus control apparatus 2 reconfigures the three-dimensional rotation displacement corrected transmission image corrected from the plurality of transmission images picked up by the used diagnosis X-ray source and the brightness corrected transmission image corrected by using the brightness conversion function from the transmission images picked up by using the diagnosis X-ray sources except for the used source into the three-dimensional data of the patient 43.

According to the operation for generating such three-dimensional data, in the same manner as the radio tomography imaging method in the above-mentioned embodiment, degradation of the image quality caused by the sensitivity difference between the plurality of imaging systems can be minimized, and simultaneously the pick-up time of the plurality of transmission images required to form the three-dimensional data can be shortened without increasing the rotation speed of the traveling gantry 14. As the result, the operation for generating such three-dimensional data can reduce a period of time when the patient has to stop the breathing, and can reduce a strain of the patient in the pick-up of a plurality of required transmission images, and can increase the number of patients who can accept the therapy.

The invention claimed is:

1. A radio tomography imaging method comprising:
    picking up a first calibration transmission image by using a first calibration radiation emitted from a first radiation source supported by a movable gantry;
    picking up a second calibration transmission image by using a second calibration radiation emitted from a second radiation source supported by said moveable gantry;
    calculating a conversion function based on the first calibration transmission image and the second calibration transmission image;
    picking up a plurality of first reconfiguration transmission images by using a plurality of first reconfiguration radiations emitted from said first radiation source when said first radiation source is positioned at a plurality of first positions different from each other, respectively;
    picking up a plurality of second reconfiguration transmission images by using a plurality of second reconfiguration radiations emitted from said second radiation source when said second radiation source is positioned at a plurality of second positions different from each other, respectively;
    correcting the plurality of second reconfiguration transmission images into a plurality of corrected transmission images based on the conversion function; and
    reconfiguring the plurality of first reconfiguration transmission images and the plurality of corrected transmission images into three-dimensional data,
    wherein a position at which said second radiation source is positioned when the second calibration radiation has been emitted coincides with a position at which said first radiation source is positioned when the first calibration radiation has been emitted,
    wherein said first radiation source emits a radiation when the second calibration radiation is emitted,
    wherein said second radiation source emits a radiation when the first calibration radiation is emitted, and
    wherein a plurality of first times when the plurality of first reconfiguration radiations are respectively emitted coincide with a plurality of second times when the plurality of second reconfiguration radiations are emitted, respectively.

2. The radio tomography imaging method according to claim 1, wherein the plurality of first reconfiguration radiations include the first calibration radiation.

3. The radio tomography imaging method according to claim 2, wherein the plurality of second reconfiguration transmission images are corrected into the plurality of corrected transmission images through brightness conversion.

4. The radio tomography imaging method according to claim 3, wherein a frequency distribution in brightness of the transmission image obtained by correcting the second calibration transmission image based on the conversion function coincides with a frequency distribution in brightness of the first calibration transmission image.

5. The radio tomography imaging method according to claim 2, further comprising:
  picking up another first calibration transmission image by using another first calibration radiation emitted from said first radiation source; and
  picking up another second calibration transmission image by using another second calibration radiation emitted from said second radiation source,
  wherein a position at which said second radiation source is positioned when said another second calibration radiation has been emitted is different from a position at which said first radiation source is positioned when the first calibration radiation has been emitted, and coincides with a position at which said first radiation source is positioned when said another first calibration radiation has been emitted,
  wherein said first radiation source emits a radiation when said another second calibration radiation has been emitted,
  wherein said second radiation source emits a radiation when said another first calibration radiation has been emitted, and
  wherein the conversion function is calculated based on said another first calibration transmission image and said another second calibration transmission image, in addition to the first calibration transmission image and the second calibration transmission image.

6. The radio tomography imaging method according to claim 1, wherein the first calibration transmission image is picked up separately from the plurality of first reconfiguration transmission images.

7. The radio tomography imaging method according to claim 6, wherein a plurality of the first calibration transmission images are picked up by using a plurality of the first calibration radiations emitted from said first radiation source when said first radiation source is positioned at the plurality of second positions, respectively,
  wherein a plurality of the second calibration transmission images are picked up by using a plurality of the second calibration radiations emitted from said second radiation source when said second radiation source is positioned at the plurality of second positions, respectively,
  wherein said first radiation source emits a radiation when each of the plurality of second calibration radiations has been emitted,
  wherein said second radiation source emits a radiation when each of the plurality of first calibration radiations has been emitted, and
  wherein one of the plurality of second reconfiguration transmission images picked up when said second radiation source is positioned at a predetermined position is corrected based on the conversion function which is calculated based on one of the plurality of first calibration transmission images picked up when said first radiation source is positioned at the predetermined position, and one of the plurality of second calibration transmission images picked up when said second radiation source is positioned at the predetermined position.

8. The radio tomography imaging method according to claim 1, further comprising:
  picking up a third calibration transmission image by using a third calibration radiation emitted from a third radiation source supported by said moveable gantry;
  picking up a fourth calibration transmission image by using a fourth calibration radiation emitted from said second radiation source;
  calculating another conversion function based on the third calibration transmission image and the fourth calibration transmission image;
  picking up a plurality of third reconfiguration transmission images by using a plurality of third reconfiguration radiations emitted from said third radiation source when said third radiation source is positioned at a plurality of third positions different from each other, respectively; and
  correcting the plurality of third reconfiguration transmission images into a plurality of other corrected transmission images based on the conversion function and the another conversion function,
  wherein a position at which said second radiation source is positioned when the fourth calibration radiation has been emitted coincides with a position at which said third radiation source is positioned when the third calibration radiation has been emitted,
  wherein said first radiation source emits a radiation when the third calibration radiation is emitted,
  wherein said second radiation source emits a radiation when the third calibration radiation is emitted,
  wherein said third radiation source emits a radiation when the first calibration radiation is emitted, and emits a radiation when the second calibration radiation is emitted,
  wherein a plurality of third times when the plurality of third reconfiguration radiations are emitted coincide with the plurality of first times, respectively, and
  wherein the three-dimensional data is reconfigured from the plurality of first reconfiguration transmission images, the plurality of corrected transmission images, and the plurality of other corrected transmission images.

9. The radio tomography imaging method according to claim 1, wherein a time period during which the plurality of first reconfiguration radiations and the plurality of second reconfiguration radiations are emitted includes a time period during which a therapeutic radiation is irradiated to a target in the plurality of first reconfiguration transmission images and the plurality of second reconfiguration transmission images.

10. A radiotherapy apparatus control apparatus controls a radiotherapy apparatus which comprises a first radiation source supported by a movable traveling gantry, and a second radiation source supported by the movable traveling gantry, said radiotherapy apparatus control apparatus comprising:
  a calibrating section configured to calculate a conversion function based on a first calibration transmission image picked up by using a first calibration radiation emitted from said first radiation source and a second calibration transmission image picked up by using a second calibration radiation emitted from said second radiation source;
  an imaging control section configured to pick up a plurality of first reconfiguration transmission images by using a plurality of first reconfiguration radiations emitted from said first radiation source when said first radiation source is positioned at a plurality of first positions different from each other, and pick up a plurality of second reconfiguration transmission images by using a plurality of second reconfiguration radiations emitted from said second radiation source when said second radiation source is positioned at a plurality of second positions different from each other, respectively;

a correcting section configured to correct the plurality of second reconfiguration transmission images into a plurality of corrected transmission images based on the conversion function, respectively; and a re-configuring section configured to reconfigure the plurality of first reconfiguration transmission images and the plurality of corrected transmission images into three-dimensional data, wherein a position at which said second radiation source is positioned when the second calibration radiation has been emitted coincides with a position at which said first radiation source is positioned when the first calibration radiation has been emitted, wherein said first radiation source emits a radiation when the second calibration radiation is emitted, wherein said second radiation source emits a radiation when the first calibration radiation is emitted, and wherein a plurality of first times when the plurality of first reconfiguration radiations are emitted coincide with a plurality of second times when the plurality of second reconfiguration radiations are emitted, respectively.

11. The radiotherapy apparatus control apparatus according to claim 10, wherein said correcting section corrects the plurality of second reconfiguration transmission images into the plurality of corrected transmission images through brightness conversion of the plurality of second reconfiguration transmission images.

12. The radiotherapy apparatus control apparatus according to claim 11, wherein a frequency distribution in brightness of the transmission image corrected from the second calibration transmission image based on the conversion function coincides with a frequency distribution in brightness of the first calibration transmission image.

13. The radiotherapy apparatus control apparatus according to claim 12, further comprising:

a third radiation source supported by said movable traveling gantry, wherein said calibrating section calculates another conversion function based on a third calibration transmission image picked up by using a third calibration radiation emitted from said third radiation source, and a fourth calibration transmission image picked up by using a fourth calibration radiation emitted from said second radiation source, wherein a position at which said second radiation source is positioned when the fourth calibration radiation is emitted coincides with a position at which said third radiation source is positioned when the third calibration radiation is emitted, wherein said first radiation source emits a radiation when the third calibration radiation is emitted, wherein said second radiation source emits a radiation when the third calibration radiation is emitted, wherein said third radiation source emits a radiation when the first calibration radiation is emitted, and emits a radiation when the second calibration radiation is emitted, wherein said imaging control section picks up a plurality of third reconfiguration transmission images by using a plurality of third reconfiguration radiations emitted from said third radiation source when said third radiation source is positioned at a plurality of third positions different from each other, respectively, wherein a plurality of third times when the plurality of third reconfiguration radiations are emitted coincide with the plurality of first times, respectively, wherein said correcting section corrects the plurality of third reconfiguration transmission images into a plurality of other corrected transmission images based on the conversion function and the another conversion function, respectively, and wherein said re-configuring section reconfigures the three-dimensional data from the plurality of first reconfiguration transmission images, the plurality of corrected transmission images, and the plurality of other corrected transmission images.

14. A radiotherapy system comprising:

a radiotherapy apparatus; and a radiotherapy apparatus control apparatus configured to control said radiotherapy apparatus, wherein said radiotherapy apparatus comprises:

a first radiation source supported by a movable traveling gantry; and a second radiation source supported by the movable traveling gantry, wherein said radiotherapy apparatus control apparatus comprises:

a calibrating section configured to calculate a conversion function based on a first calibration transmission image picked up by using a first calibration radiation emitted from said first radiation source and a second calibration transmission image picked up by using a second calibration radiation emitted from said second radiation source;

an imaging control section configured to pick up a plurality of first reconfiguration transmission images by using a plurality of first reconfiguration radiations emitted from said first radiation source when said first radiation source is positioned at a plurality of first positions different from each other, and pick up a plurality of second reconfiguration transmission images by using a plurality of second reconfiguration radiations emitted from said second radiation source when said second radiation source is positioned at a plurality of second positions different from each other, respectively;

a correcting section configured to correct the plurality of second reconfiguration transmission images into a plurality of corrected transmission images based on the conversion function, respectively; and a re-configuring section configured to reconfigure the plurality of first reconfiguration transmission images and the plurality of corrected transmission images into three-dimensional data, wherein a position at which said second radiation source is positioned when the second calibration radiation has been emitted coincides with a position at which said first radiation source is positioned when the first calibration radiation has been emitted, wherein said first radiation source emits a radiation when the second calibration radiation is emitted, wherein said second radiation source emits a radiation when the first calibration radiation is emitted, and wherein a plurality of first times when the plurality of first reconfiguration radiations are emitted coincide with a plurality of second times when the plurality of second reconfiguration radiations are emitted, respectively.

15. The radiotherapy system according to claim 14, wherein said radiotherapy apparatus further comprises:
    a therapeutic radiation irradiating unit configured to irradiate a therapeutic radiation to a target in the plurality of first reconfiguration transmission images and the plurality of second reconfiguration transmission images.

* * * * *